US009182886B2

(12) United States Patent
Schultz et al.

(10) Patent No.: US 9,182,886 B2
(45) Date of Patent: Nov. 10, 2015

(54) CHROMATOGRAPHY CONFIGURATION INTERFACE

(71) Applicant: BIO-RAD LABORATORIES, INC., Hercules, CA (US)

(72) Inventors: Christof Schultz, Orinda, CA (US); Dominic Casenas, Union City, CA (US); Farah Mavandadi, San Mateo, CA (US)

(73) Assignee: Bio-Rad Laboratories Inc., Hercules, CA (US)

( * ) Notice: Subject to any disclaimer, the term of this patent is extended or adjusted under 35 U.S.C. 154(b) by 327 days.

(21) Appl. No.: 13/675,022

(22) Filed: Nov. 13, 2012

(65) Prior Publication Data

US 2013/0132897 A1    May 23, 2013

Related U.S. Application Data

(60) Provisional application No. 61/559,399, filed on Nov. 14, 2011.

(51) Int. Cl.
  *G06F 3/048* (2013.01)
  *G06F 3/0482* (2013.01)
  *G01N 35/00* (2006.01)
  *G01N 30/88* (2006.01)
  *G01N 30/86* (2006.01)

(52) U.S. Cl.
  CPC .............. *G06F 3/0482* (2013.01); *G01N 30/88* (2013.01); *G01N 35/00722* (2013.01); *G01N 30/8662* (2013.01); *G01N 2030/8881* (2013.01); *G01N 2035/0091* (2013.01)

(58) Field of Classification Search
  CPC .................. G01N 2035/0091; G01N 30/8662; G06F 8/34; G06F 3/0481; G06F 3/04847; G05B 19/0426; G05B 2219/23258
  USPC ......................................................... 715/771
  See application file for complete search history.

(56) References Cited

U.S. PATENT DOCUMENTS 5,588,109 A * 12/1996 Dickinson et al. ............ 715/740
5,801,699 A *  9/1998 Hocker et al. ................ 715/837

(Continued)

OTHER PUBLICATIONS

International Search Report and Written Opinion of PCT/US2012/65015 mailed on Mar. 26, 2013, 28 pages.

*Primary Examiner* — Boris Pesin
*Assistant Examiner* — Mandrita Brahmachari
(74) *Attorney, Agent, or Firm* — Kilpatrick Townsend & Stockton LLP

(57) ABSTRACT

Systems and methods that facilitate the setup and visualization of a configurable process, for example a chromatography experiment to be conducted using a configurable chromatography system. A user interface displays category regions representing sections of a process, and displays a plurality of selectable items representing components appropriate for placement in the category regions. A user interface control causes selection of one of the selectable items and placement of the selected item into one of the category regions, to define a selected process configuration. The user interface control may be a scrolling control that causes a set of selectable items appropriate for placement in the respective category region to scroll through the category region. When the computer displaying the user interface is also connected to the system being configured, the user interface may also facilitate setup, monitoring, and control of the resulting process.

22 Claims, 15 Drawing Sheets

(56) References Cited

U.S. PATENT DOCUMENTS

| | | | |
|---|---|---|---|
| 7,770,125 B1* | 8/2010 | Young et al. | 715/764 |
| 8,701,012 B1* | 4/2014 | Selman et al. | 715/738 |
| 2003/0001898 A1* | 1/2003 | Bernhardson | 345/786 |
| 2004/0143402 A1 | 7/2004 | Colinge et al. | |
| 2006/0027490 A1* | 2/2006 | DeMarco | 210/198.2 |
| 2008/0233018 A1* | 9/2008 | van Dam et al. | 422/159 |
| 2010/0101411 A1* | 4/2010 | Tipler | 95/86 |
| 2011/0258566 A1* | 10/2011 | Oustiougov et al. | 715/766 |
| 2012/0005604 A1* | 1/2012 | Wirch et al. | 715/765 |

* cited by examiner

CHROMATOGRAPHY CONFIGURATION INTERFACE

This application claims priority to provisional U.S. Patent Application 61/559,399, filed Nov. 14, 2011 and titled "Chromatography Configuration Interface", the entire disclosure of which is hereby incorporated by reference herein.

BACKGROUND OF THE INVENTION

Chromatography is an analytical technique for separating components of a chemical mixture. Chromatography may be used for the identification, extraction, and purification of species of interest, for example proteins, peptides, nucleic acids, monoclonal antibodies, or other species of interest in biological research and analysis, or drug manufacturing. Chromatography may be used in many other applications as well. These techniques have reached such a high level of sophistication that virtually any biological species can be obtained in a highly purified form.

However, different species may require different processes for isolation, for example different sample preparation methods, different separation media, and different conditions under which separation is performed. Accordingly, configurable chromatography systems have been developed, in which varying components may be selected and interconnected in varying ways for the performance of different separations.

BRIEF SUMMARY OF THE INVENTION

Embodiments of the invention provide systems and methods that facilitate the setup and visualization of a configurable process, for example a chromatography experiment to be conducted using a configurable chromatography system.

According to one aspect, a graphical user interface for selecting from a plurality of available process configurations includes a plurality of adjacent displayed category regions representing sections of a process, and a plurality of selectable items representing components appropriate for placement in the category regions. The graphical user interface further includes a control that causes selection of one of the selectable items and placement of the selected item into one of the category regions. The set of items currently selected in the plurality of category regions defines a selected process configuration. In some embodiments, when one of the selectable items is selected, candidate locations are indicated within the category regions where the particular selected item would be appropriately placed. In some embodiments, the control comprises, for each of the category regions, a scrolling control that causes a set of selectable items appropriate for placement in the respective category region to scroll through the category region. The category regions may be arranged horizontally. The scrolling control for each category region may cause the items for the respective category region to scroll circularly. In some embodiments, the graphical user interface comprises, for each of the displayed category regions, two scrolling controls that cause the selectable items appropriate for placement in the respective category region to scroll through the respective category region, the first control causing the selectable items to scroll through the respective category region in a first direction, and the second control causing the selectable items to scroll through the respective category region in a second direction opposite the first. In some embodiments, the category regions represent respective sections of a flow diagram for a chromatography system, and the selectable items graphically represent components of a chromatography system appropriate for placement in the respective sections. In some embodiments, the graphical user interface comprises five category regions corresponding to the following sections of a flow diagram for a chromatography system: pumps, sample injection, columns, detectors, and sample collection. In some embodiments, the graphical user interface further comprises, during operation of a chromatography system represented in the graphical user interface by a selected configuration, status information about the operation of one or more components of the chromatography system displayed adjacent the corresponding representations of the one or more components in the graphical user interface. In some embodiments, upon designation of a particular category region, items appropriate for inclusion in the designated category region are presented to the user for selection.

According to another aspect, a computer system comprises a processor, a display device, a user input device, and a memory holding instructions. When executed by the processor, the instructions cause the computer to display, on the display device: a plurality of adjacent category regions representing sections of a process; a plurality of selectable items representing components appropriate for placement in the category regions, and a control that causes selection of one of the selectable items and placement of the selected item into one of the category regions. The set of items currently selected in the plurality of category regions defines a selected process configuration.

According to another aspect, a system comprises a chromatography system including a plurality of fluid manipulation components configurable into a chromatography flow scheme, and a computer system coupled to the chromatography system. The computer system includes a processor, a display device, a user input device, and a memory holding instructions. When executed by the processor, the instructions cause the computer to display, on the display device, a plurality of adjacent category regions representing sections of a chromatography flow scheme, a plurality of selectable items representing fluid manipulation components appropriate for placement in the category regions, and a control. The control, in response the user input device, causes selection of one of the selectable items and placement of the selected item into one of the category regions. The set of items currently selected in the plurality of category regions defines a selected fluidic scheme. In some embodiments, the selected fluidic scheme matches the configuration of the chromatography system. In some embodiments, the control comprises, for each of the category regions, a scrolling control that causes a set of selectable items appropriate for placement in the respective category region to scroll through the category region. In some embodiments, the instructions further cause the computer system to display, during operation of the chromatography system, status information about the operation of one or more of the fluid manipulation components, and the status information is displayed adjacent the corresponding representations of the one or more fluid manipulation components. In some embodiments, the instructions further cause the computer system to guide a user of the system in making fluidic connections among the plurality of fluid manipulation components. In some embodiments, the instructions further cause the computer system to communicate to at least one of the fluid manipulation components an instruction to visibly indicate a point of connection for a fluidic connection. In some embodiments, the instructions further cause the computer system to interact with the plurality of fluid manipulation components to identify the fluid manipulation components, and to map in a data structure at least one of the fluid manipulation components with a particular item in the selected fluidic scheme. In some embodiments, the instructions further cause the computer system to indicate in a graphical user interface at least one ambiguity in the mapping of fluid manipulation components to items in the graphical user interface.

According to another aspect, a graphical user interface for mapping components of a chromatography system to a representation of a fluidic scheme comprises a representation of the fluidic scheme including representations of a plurality of fluid manipulation components needed to implement the fluidic scheme, a representation of a chromatography system that includes a plurality of actual fluid manipulation components, and an indication of at least one ambiguity in the mapping of the actual fluid manipulation components to the fluid manipulation component representations. In some embodiments, the at least one ambiguity arises from the inclusion of multiple identical fluid manipulation components in the fluidic scheme. The graphical user interface may further include a user interface device that enables a user to resolve the at least one ambiguity. In some embodiments, the user interface device enables the user to drag a representation of a fluid manipulation component from the representation of the fluidic scheme to the representation of the chromatography system, or the user interface component enables the user to drag a representation of a fluid manipulation component from the representation of the chromatography system to the representation of the fluidic scheme chromatography system, or both.

DETAILED DESCRIPTION OF THE INVENTION

Figure 1:
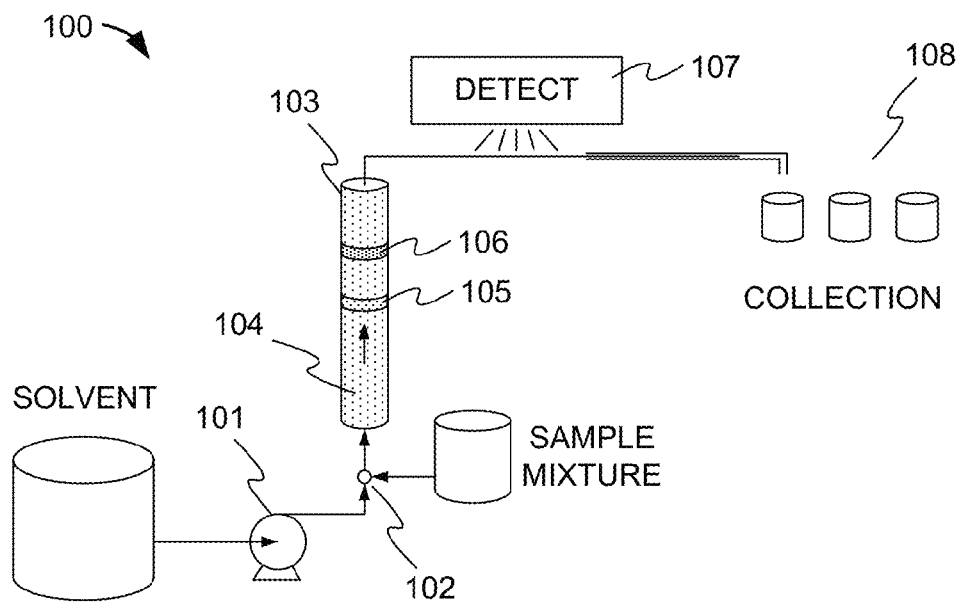
FIG. 1 illustrates a simplified schematic view of a chromatography process with which embodiments of the invention may find utility.

FIG. 1 illustrates a simplified schematic view of a chromatography process 100 with which embodiments of the invention may find utility. In the example process 100, a pump 101 propels a solvent through the system. At a sample injector 102, a burst of the mixture to be analyzed is injected into the stream of solvent, and the mixture and solvent are carried through a column 103. Column 103 is filled with a stationary medium 104. Medium 104 is selected such that different components of the mixture have differing affinities to or interactions with the medium. As the solvent and mixture travel through column 104, different components 105, 106 of the mixture will travel at different rates through the column, and will thus become separated.

A detector 107 detects when the different components 105, 106 pass the detector, and the components are separately directed to different sample collection areas. Thus, components of the original sample mixture can be separated and purified. While separation of mixtures is one common use of chromatography, other uses are possible.

Figure 2:
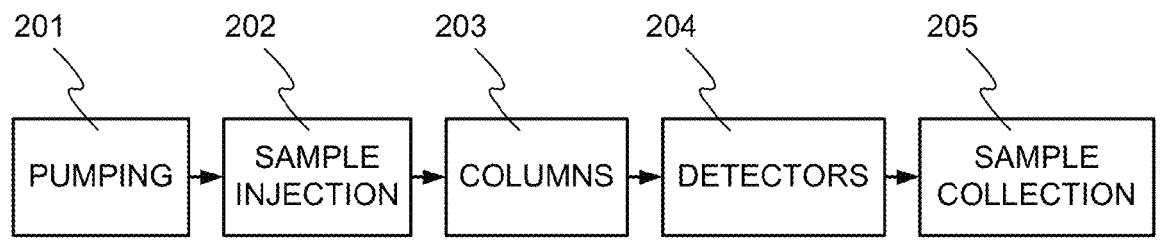
FIG. 2 illustrates stages in the chromatography process of FIG. 1.

Liquid chromatography generally includes the five stages shown in FIG. 2 and represented by blocks 201-205. However, within this basic framework, many, many variations are possible. For example, depending on the sample being analyzed, different solvents may be used, or multiple solvents may be used and pumped separately. Multiple columns may be utilized, for example in series to provide a longer flow path and greater separation between similar mixture components for enhanced detection and separation or in succession when different techniques are required. Different detectors may be used, depending on the characteristics of the components of interest. For example, components 105, 106 may be distinguished by detector 107 based on differences in their color, refractive index, spectral absorption characteristics, pH, or other characteristics.

Multiple different options are available for the equipment used in each of the five stages. For maximal flexibility in experiment design, configurable chromatography systems have been developed. Examples of such systems are described in co-pending U.S. Provisional Patent Application No. 61/526,959, filed Aug. 24, 2011 and titled "Modular Automated Chromatography System", the entire disclosure of which is hereby incorporated by reference herein.

Figure 3:
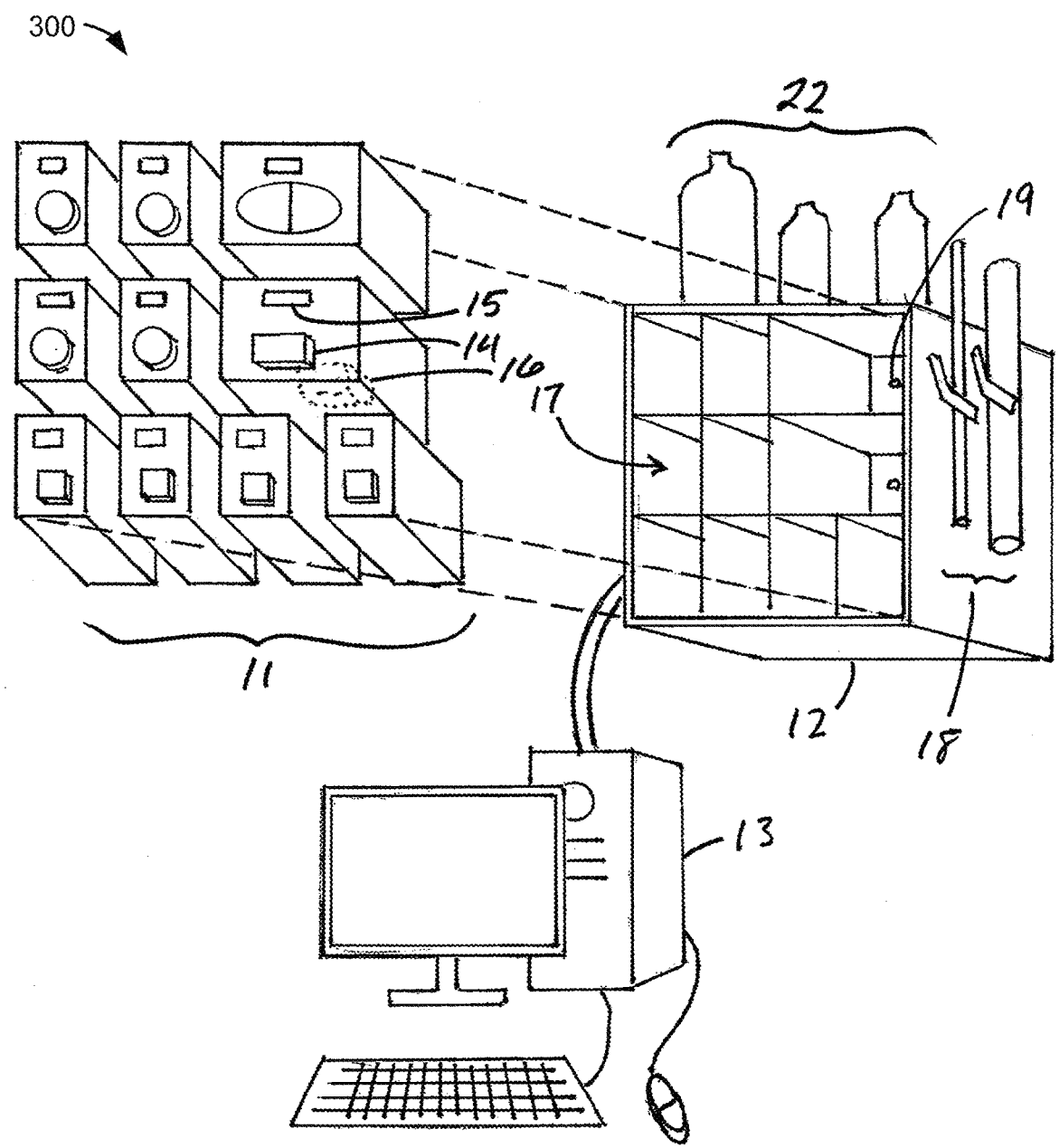
FIG. 3 illustrates an example of a configurable chromatography system, with which embodiments of the invention may find utility.

FIG. 3 illustrates an example of a configurable chromatography system 300, with which embodiments of the invention may find utility. Configurable chromatography system 300 includes a plurality of modules 11 poised in front of a base unit or mounting frame 12, which is connected to a computer 13. Each module 11 may include a fluid manipulation component 14, an alarm indicator 15, and a microcontroller 16. Computer 13 may assist in any of the setup, monitoring, and control of the system, and may be connected to other chromatography systems as well. The different modules 11 may represent different pumping units, sample injectors, detectors, or other equipment for use in other parts of the chromatography process. Mounting frame 12 includes a series of bays 17 into which the modules can be placed, and a column rack 18 for holding columns. Each bay includes an electrical connector 19 for making electrical contact with electronics inside the modules 11 and communicating with microcontroller 16 in the respective bay 17. Reservoirs 22 are provided in a convenient location, for example on the top of mounting frame 12, for holding various solvents, buffers, wash liquids, and the like. The modules, columns, and reservoirs may be plumbed together in the proper configuration for a particular experiment using tubing (not shown), for example around, behind, or in front of mounting frame 12.

While the placement and interconnections of the various parts of a chromatography system may be in any required or practical arrangement, including three-dimensional arrangements, it is useful to conceptualize any chromatography experiment in the sequential linear arrangement depicted in FIG. 2.

Figure 4:
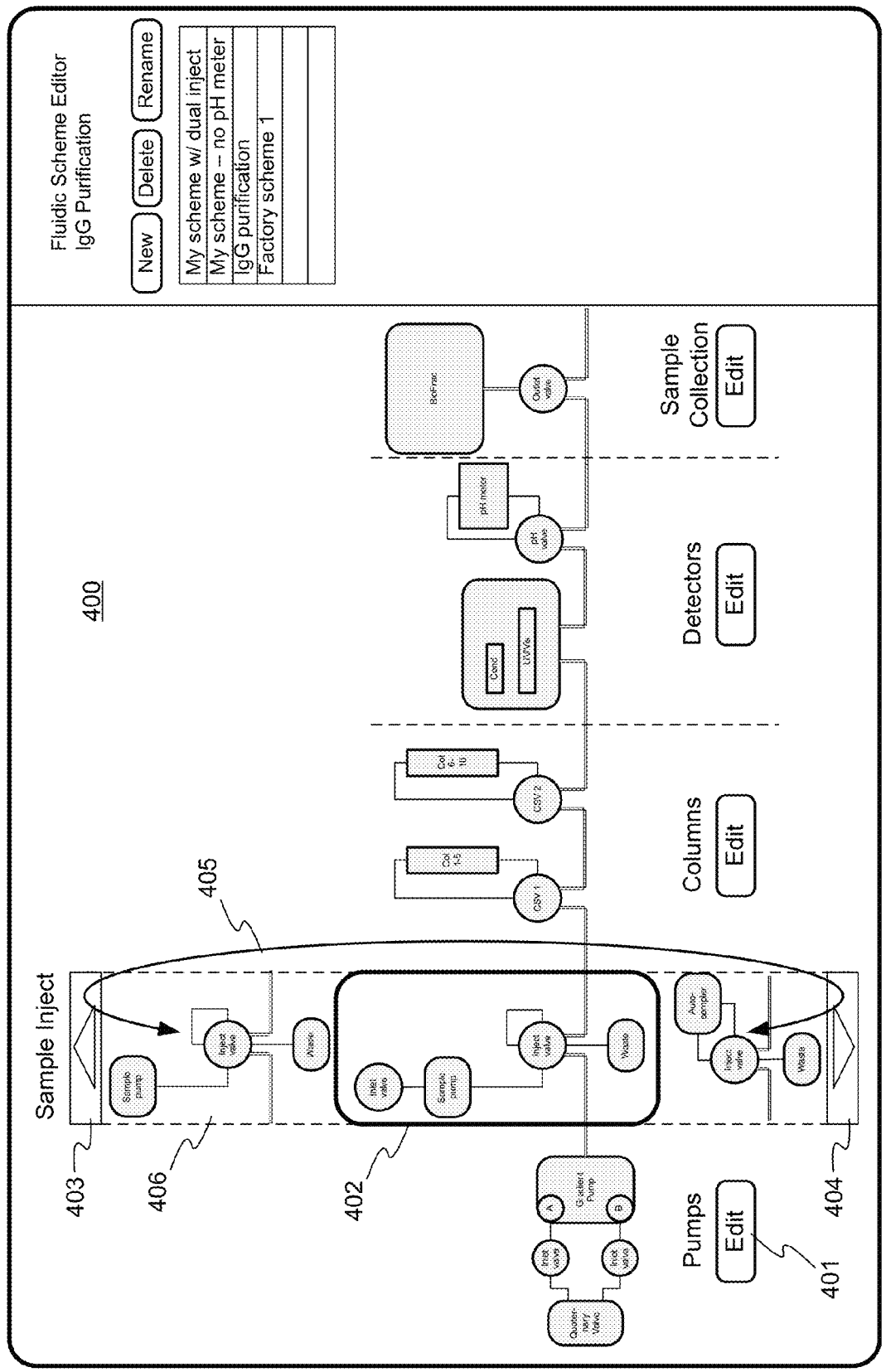
FIG. 4 illustrates a graphical user interface in accordance with an embodiment of the invention for selecting from a plurality of available process configurations, such as for the chromatography system of FIG. 3.

According to an embodiment of the invention, this sequential linear conceptualization may be exploited to simplify and make intuitive the modeling and setup of a chromatography experiment. For example, FIG. 4 illustrates a graphical user interface 400 in accordance with an embodiment of the invention for selecting from a plurality of available process configurations, such as for chromatography system 300. Graphical user interface 400 may be presented on computer 13, or another computer system or touchscreen, and a user of the computer system may interact with graphical user interface 400 using a keyboard, mouse, trackball, stylus, or other input device or combination of input devices.

User interface 400 is divided into five category regions representing sections of the chromatography process—pumps, sample inject, columns, detectors, and sample collection. It will be recognized that in other applications, more or fewer category regions may be presented, and that the category regions may represent sections of a process other than chromatography. In four of the category regions, items have been selected or placed by default into a representation of the process. This representation may be called a fluidic scheme. Each category region includes a control for entering an editing mode, for example button 401 as shown in the "pumps" region.

Figure 5:
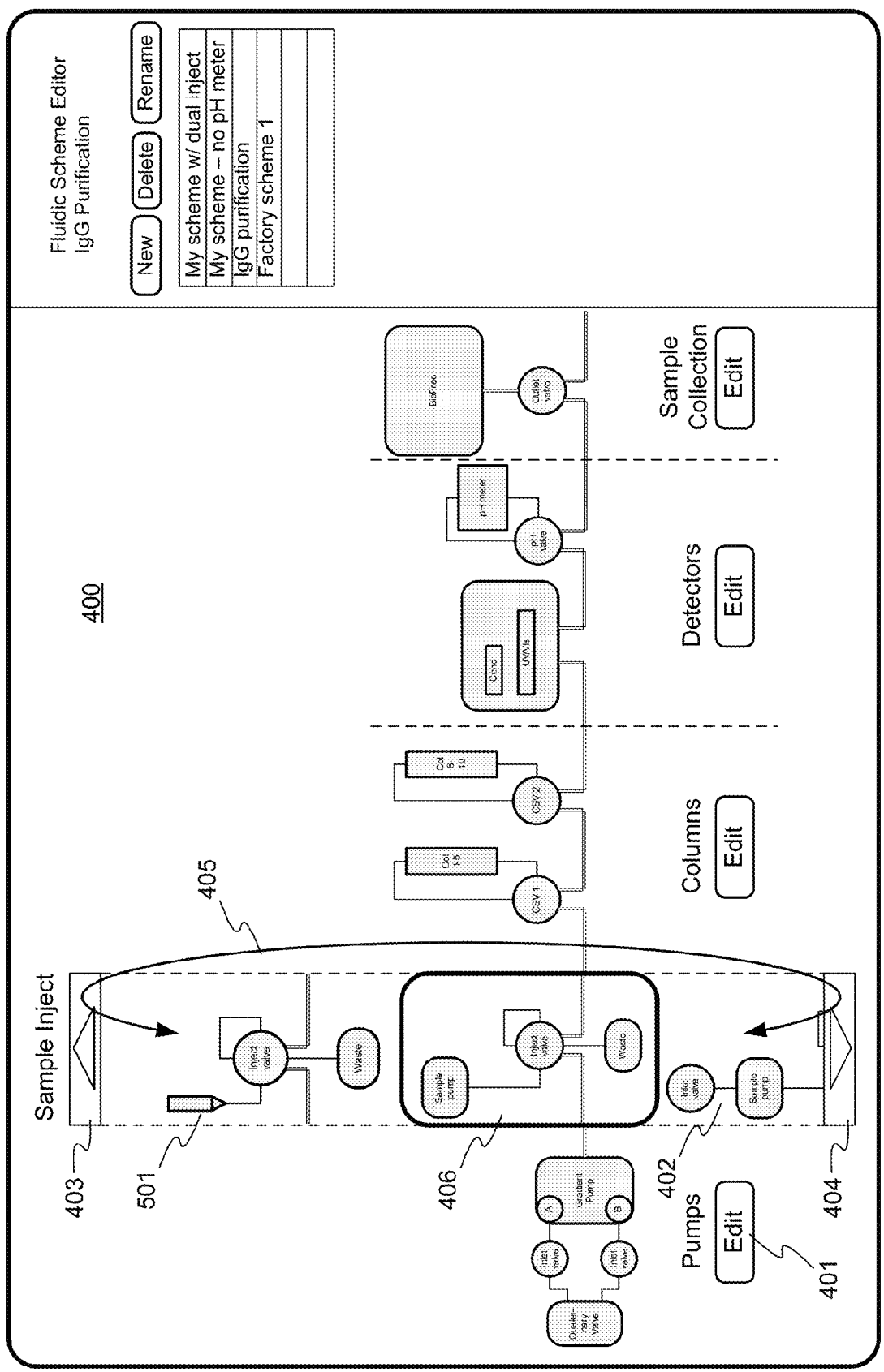
FIG. 5 illustrates the user interface of FIG. 4 as it may appear after one activation of a scrolling control.

Once the editing mode is entered for a particular region, a display such as is shown in the "sample inject" region is presented. In this example, a particular sample injection arrangement 402 has been placed into the fluidic scheme, either by default or by previous user selection. Clickable scrolling controls 403 and 404 are provided, and cause a set of selectable sample injection arrangements appropriate for placement in the sample injection category region to scroll up and down respectively through the category region, in "spinning wheel" or "slot machine" fashion, as indicated by arrow 405. The arrangement aligned with the items in the other category regions at any particular time is called a selected item for its respective category region, and the collective set of selected items may be referred to as a selected process configuration. FIG. 5 illustrates user interface 400 as it may appear after one activation of scrolling control 404, scrolling the items in the "sample inject" category downward, bringing item 406 into alignment with the items in the other regions and making item 406 the currently selected sample injection arrangement. A new sample injection arrangement, item 501, has scrolled into position above item 406.

Figure 6:
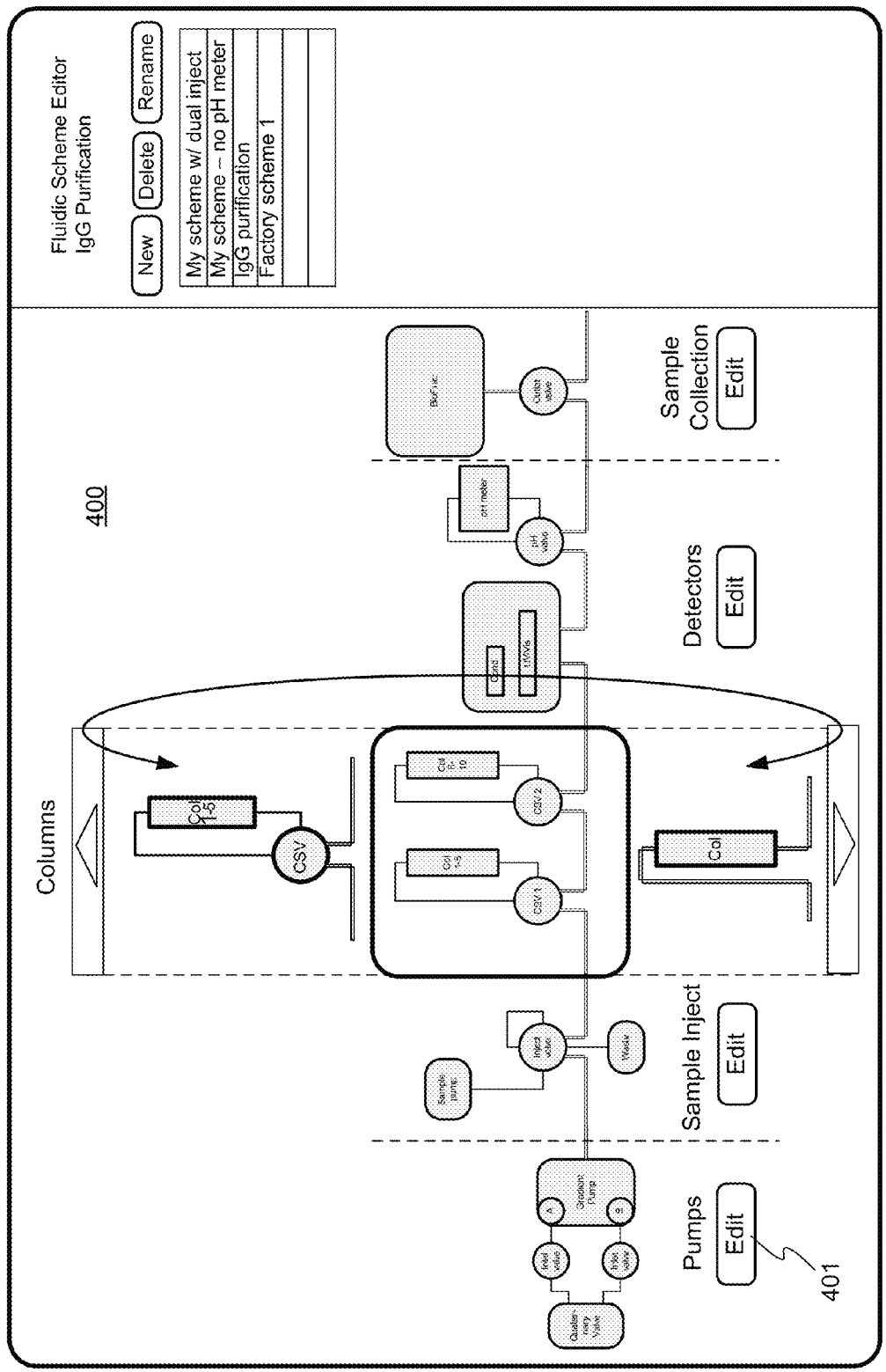
FIG. 6 illustrates the example graphical user interface of FIG. 4 configured to edit another category region.
Figure 7A:
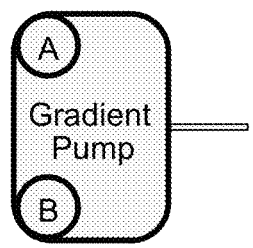
FIGS. 7A-7F illustrate a number of possible pump arrangements that may be provided as available items for a section of a fluidic scheme selected using an embodiment of the invention.
Figure 7B:
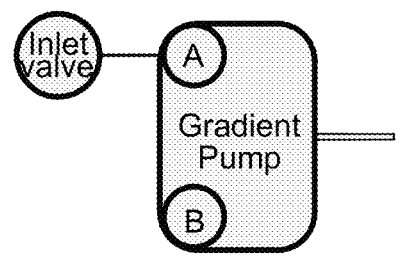
Figure 7C:
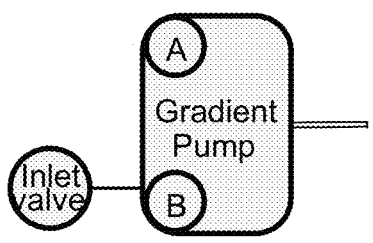
Figure 7D:
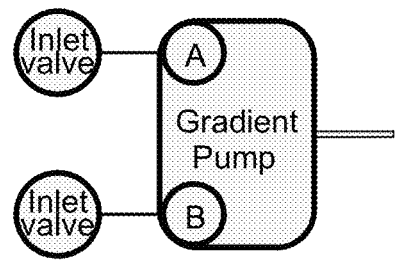
Figure 7E:
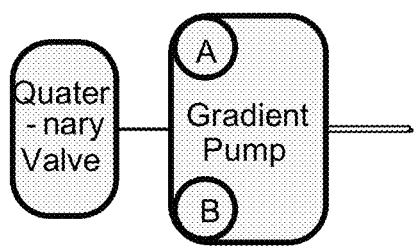
Figure 7F:
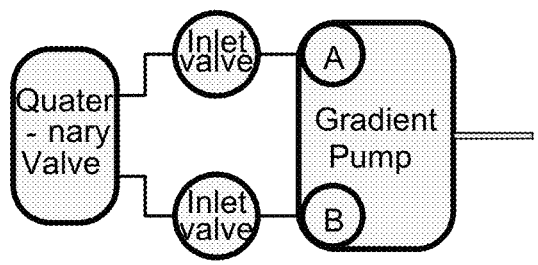
Figure 8A:
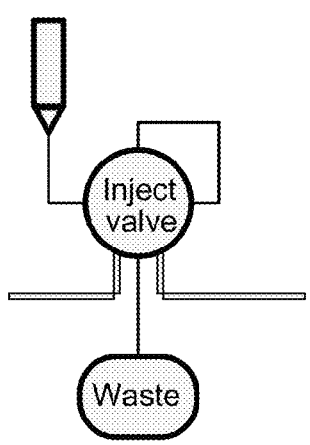
FIGS. 8A-8E illustrate a number of possible sample injection arrangements that may be provided as available items for a section of a fluidic scheme selected using an embodiment of the invention.
Figure 8B:
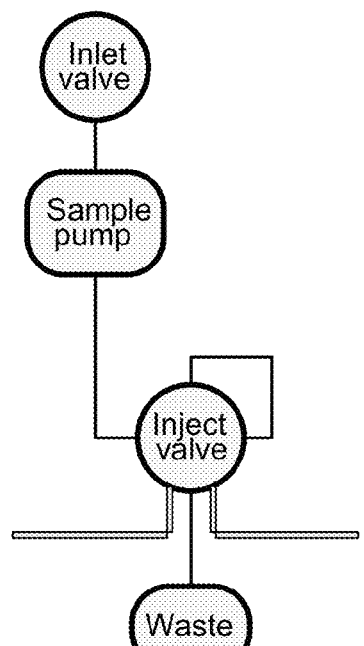
Figure 8C:
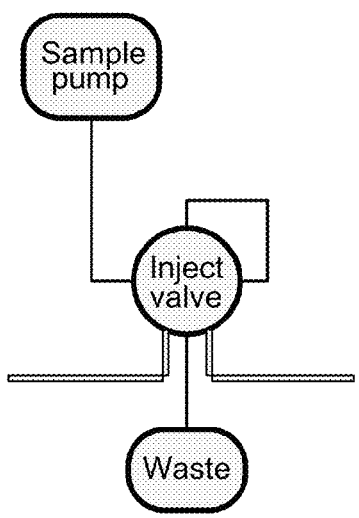
Figure 8D:
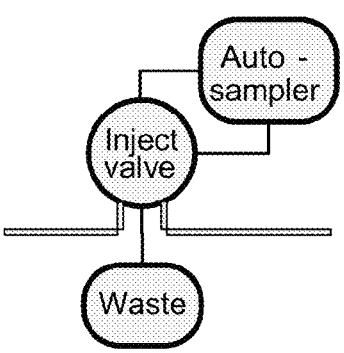
Figure 8E:
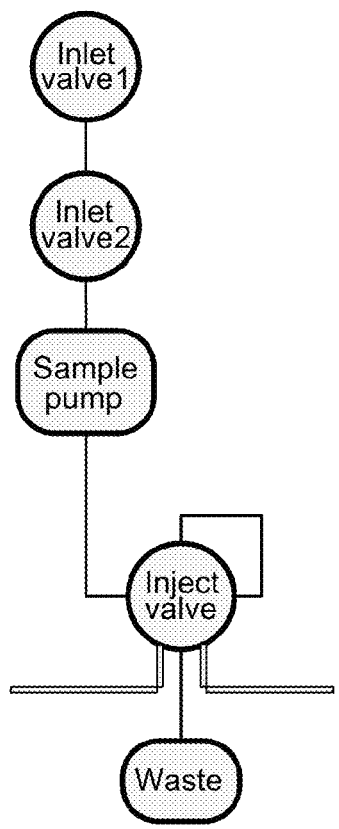
Figure 9A:
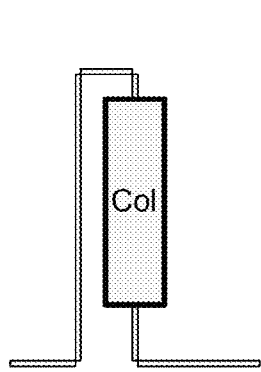
FIGS. 9A-9D illustrate a number of possible column arrangements that may be provided as available items for a section of a fluidic scheme selected using an embodiment of the invention.
Figure 9B:
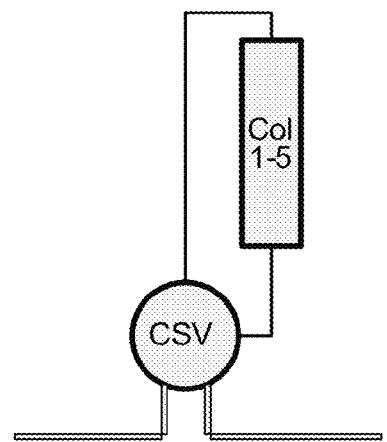
Figure 9C:
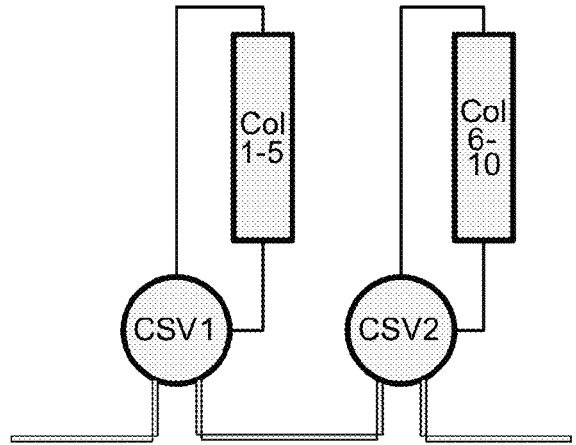
Figure 9D:
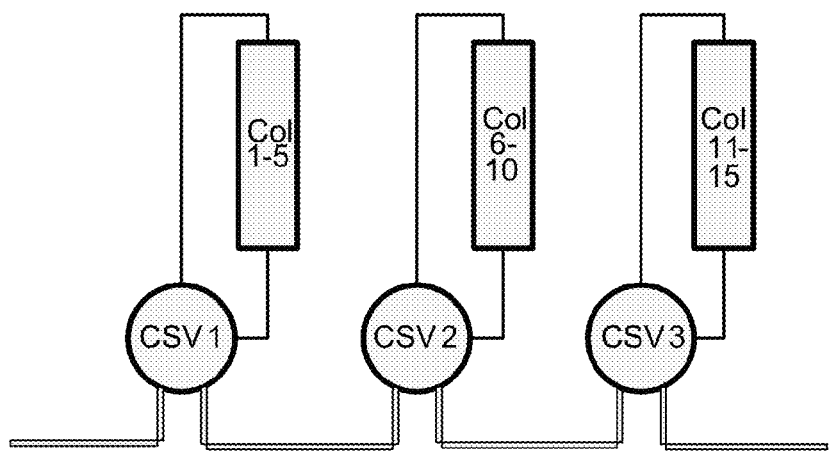
Figure 10A:
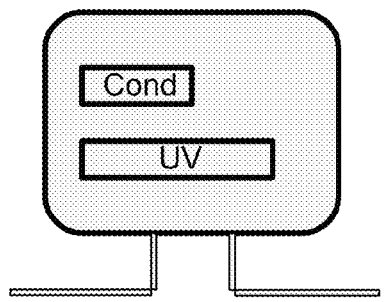
FIGS. 10A-10D illustrate a number of possible detector arrangements that may be provided as available items for a section of a fluidic scheme selected using an embodiment of the invention.
Figure 10B:
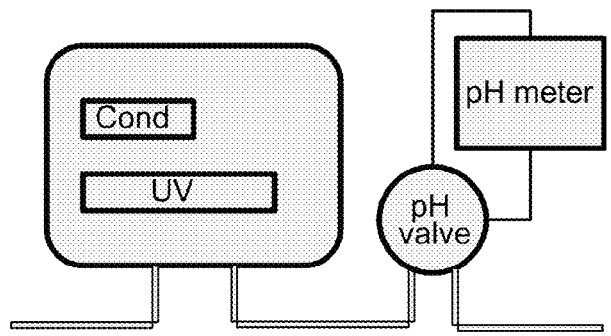
Figure 10C:
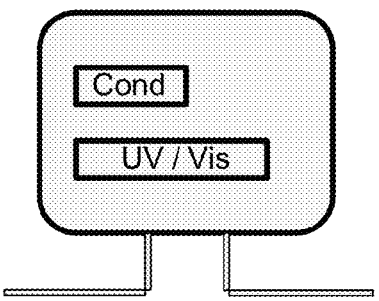
Figure 10D:
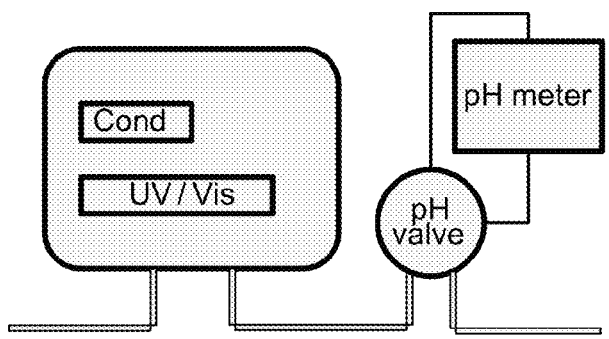
Figure 11A:
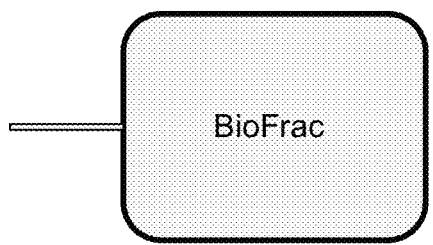
FIGS. 11A-11E illustrate a number of possible sample collection arrangements that may be provided as available items for a section of a fluidic scheme selected using an embodiment of the invention.
Figure 11B:
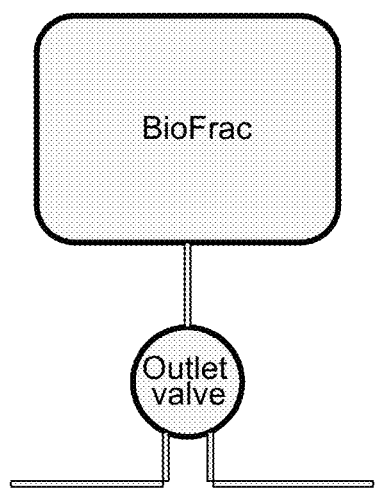
Figure 11C:
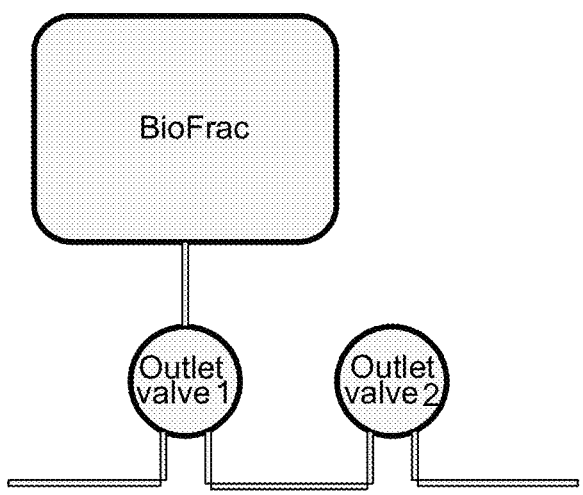
Figure 11D:
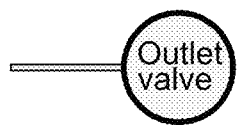
Figure 11E:
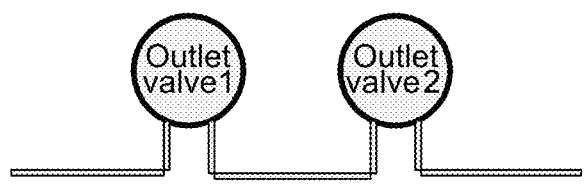

Similar scrolling controls are provided for the other category regions, representing other fluidic scheme sections. The user may edit each of the category regions in turn, in any order, and may revisit and revise his or her selections as desired, until a suitable fluidic scheme is arrived at for a desired experiment. FIG. 6 illustrates example graphical user interface 400 after the "Edit" button corresponding to the "Columns" region has been selected.

The system stores a library of available items for each of the category regions, or process sections in the example of FIG. 4. In some embodiments, scrolling controls 403 and 404 cause the available items to scroll circularly through the category region, so that the sequence of displayed items repeats indefinitely when control 403 or 404 is continuously used. In other embodiments, the scrolling may be linear, such that when all of the items have been scrolled through, the scrolling stops and it is necessary to scroll in the opposite direction to view the items again.

The category regions in example interface 400 are arranged horizontally, such that the scrolling occurs vertically, but other arrangements are possible. For example, the category regions could be arranged vertically, with items scrolling through the regions horizontally.

FIGS. 7A-7F illustrate a number of possible pump arrangements that may be provided as available items for the "Pumps" section of a fluidic scheme selected using an embodiment of the invention.

FIGS. 8A-8E illustrate a number of possible sample injection arrangements that may be provided as available items for the "Sample Inject" section of a fluidic scheme selected using an embodiment of the invention.

FIGS. 9A-9D illustrate a number of possible column arrangements that may be provided as available items for the "Columns" section of a fluidic scheme selected using an embodiment of the invention.

FIGS. 10A-10D illustrate a number of possible detector arrangements that may be provided as available items for the "Detectors" section of a fluidic scheme selected using an embodiment of the invention.

FIGS. 11A-11E illustrate a number of possible sample collection arrangements that may be provided as available items for the "Sample Collection" section of a fluidic scheme selected using an embodiment of the invention.

In other embodiments, more, fewer, or different items may be provided for selection within the category regions. As will be appreciated, a graphical user interface according to an embodiment of the invention may enable efficient selection of a fluidic scheme or other process configuration from a large number of possible configurations. For example, the example fluidic items illustrated in FIGS. 7A-11E may be combined in up to 2,400 different ways. Any of the possible combinations may be selected by scrolling each of the category regions to select one item for the respective region, in a simple and straightforward manner. In some applications, certain items may be incompatible with other items in other category regions, and the system may automatically pass over any item that is not compatible with some other already-selected item. A message may be supplied to inform the user that a potential incompatibility exists and has been avoided.

A user interface embodying the invention may be implemented on a computer such as computer 13 connected to a chromatography system such as system 300. While computer 13 is depicted as a desktop computer, any suitable computer type may be used, including a laptop or tablet computing device.

In other embodiments, a user interface embodying the invention may be implemented in a stand-alone computing device that is not connected to a chromatography system. For example, a portable computing device such as a laptop computer, tablet computer, smart phone, personal digital assistant, or other kind of computing device may be programmed to display a user interface according to an embodiment of the invention, and to enable specification of a fluidic scheme. This kind of implementation may be useful in a number of scenarios, for example a sales or experiment planning scenario. A sales representative may use a stand-alone device to assist a customer in selecting a fluidic scheme for a particular separation, to identify what equipment the customer may need to order to implement the scheme. In another example, a user interface according to embodiments may be implemented on a desktop computer used for training on the specification of fluidic schemes, without a connection to a chromatography system.

In embodiments where the computer used to select a fluidic scheme for a chromatography experiment is also connected to the configurable chromatography system used to conduct the experiment, other user interface features may be provided, in accordance with additional embodiments of the invention.

For example, once the desired process modules 11 are selected for conducting an experiment according to a selected fluid scheme, the modules must be interconnected, or "plumbed", so that the various fluids are delivered in sequence to the proper modules. A user interface according to embodiments of the invention may assist in guiding the plumbing task, so that errors may be avoided and the plumbing can be accomplished in an efficient manner. For example, a user may click on a particular flow line represented in the selected fluidic scheme, and computer 13 may communicate with the affected modules 11, which may illuminate light emitting diodes or other indicators near the connection points where tubing should be connected to physically make the plumbing connection selected in the user interface. Once the plumbing connection has been made, the user may indicate to computer 13 that the connection is completed, and the depiction in the user interface may be changed to show that connection as having been completed. For example, the user may click a second time on the same flow line, or "right click" on the depiction of the flow line and select from a menu to indicate that the corresponding physical connection is complete. Computer 13 may then change the color of the flow line in the user interface, or change its representation in some other way. In this way, the user may be presented with a visual depiction of the state of the plumbing of the system, and may be less likely to omit or mis-connect a plumbing line. Alternatively or in addition, the system may also show a tabular list of plumbing connections required for a particular system setup, with a visual indication of which connections have been completed and which have not.

A user interface in accordance with embodiments may also be used to assist in controlling the depicted chromatography system. For example, a user may be able to start and stop pumps, dispense sample, adjust pressures or flow rates, or control other aspects of an experiment by clicking on the representation of the component to be controlled in the user interface, and then entering control information. The information may be communicated by computer 13 to one or more modules 11 via the respective electrical connectors 19. In some embodiments, the system may provide automated control of the chromatography system or other process. For example, computer 13 may implement a macro language or similar programmability function, which may be configured to control the experiment.

Figure 12:
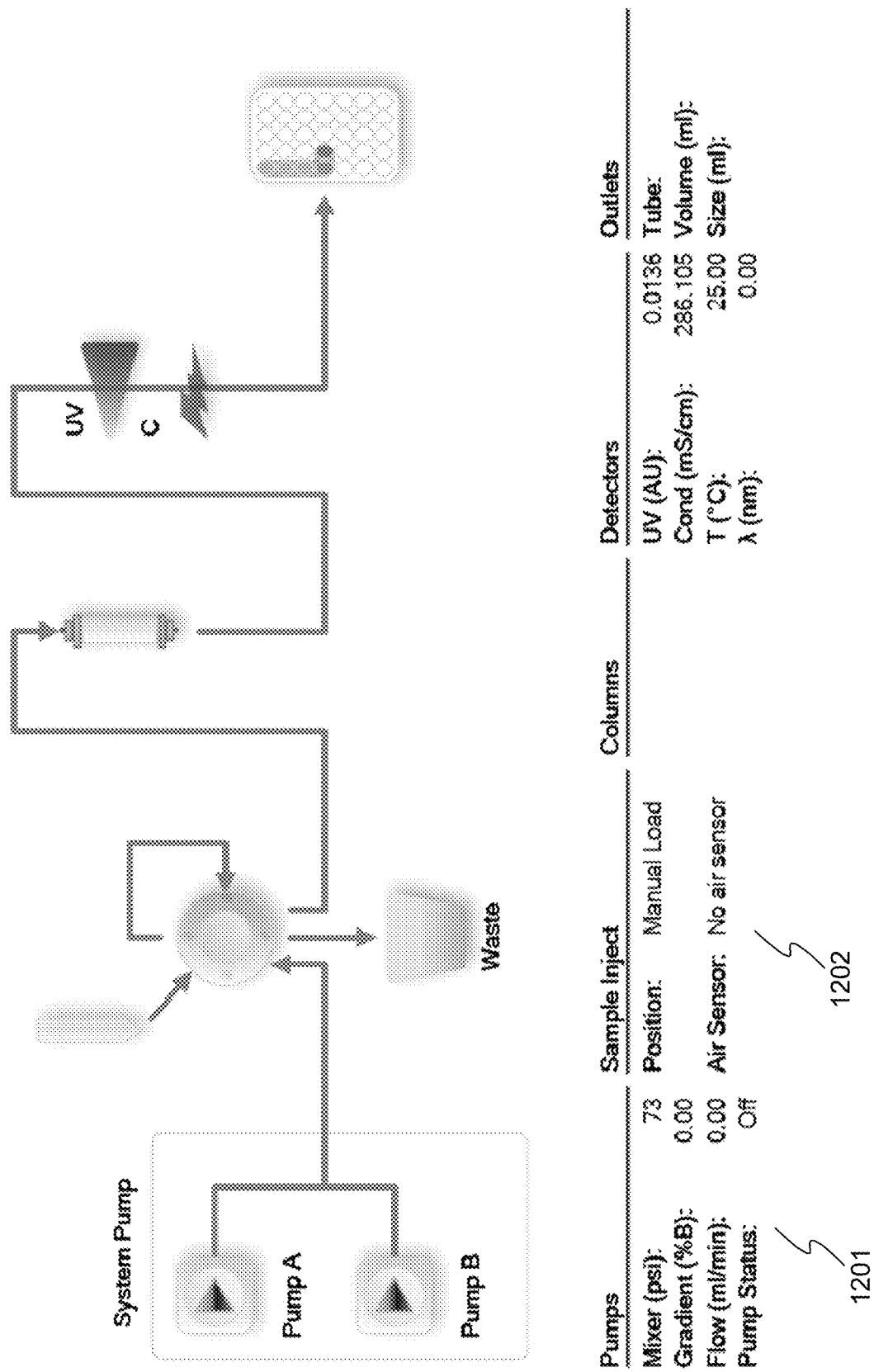
FIG. 12 illustrates a graphical user interface, according to another embodiment.

The system may also provide additional information during an experiment. FIG. 12 illustrates a graphical user interface 1200, according to another embodiment. It will be appreciated that graphical user interface 1200 depicts a fluidic scheme as may be selected by the method depicted in FIGS. 4 and 5, and while stylistically different than graphical user interface 400, includes the same five category regions holding representations of a pump arrangement, a sample injector, a column, detectors, and sample collectors. In addition, graphical user interface 1200 includes status information about the operation of one or more components of the chromatography system. The status information is displayed adjacent the corresponding representations of the system components in the graphical user interface. For example, pump status information 1201 indicates, among other things, that a mixer is operating at a pressure of 73 psi. Sample inject status information 1202 indicates, among other things, that the system is configured for manual loading. Other information may be provided for other system components as well.

Figure 13:
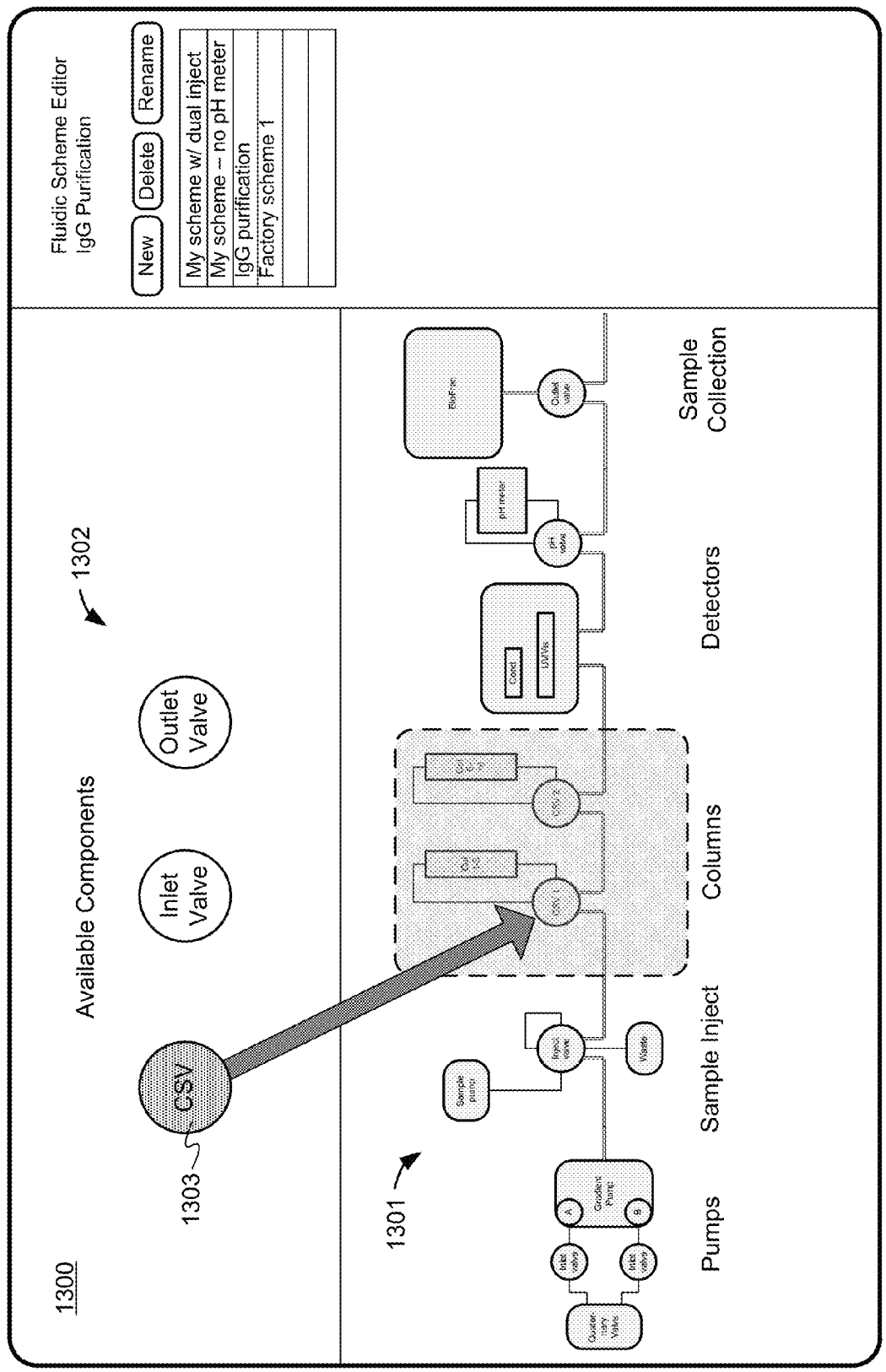
FIG. 13 illustrates a graphical user interface in accordance with another embodiment of the invention.

FIG. 13 illustrates a graphical user interface 1300 in accordance with another embodiment of the invention. In example graphical user interface 1300, a fluidic scheme 1301 is displayed for configuration. A list 1302 of available components, which may not be yet included in the fluidic scheme, is also displayed. Graphical user interface 1300 includes category regions similar to those of graphical user interface 400, but uses a different technique for placing system components in the displayed scheme. The user selects one of the components in list 1302, for example via a mouse click or other method, and can drag the selected component into the fluidic scheme. Computer 13 then highlights logical sections or "hot spots" of fluidic scheme 1301 where the selected component could be placed. In the example shown in FIG. 13, the user has selected CSV 1303, and the computer has highlighted the "Columns" region to indicate that CSV 1303 may be dragged there for addition to fluidic scheme 1301. Once the selected component is dragged into the fluidic scheme, the representation of the fluidic scheme is automatically redrawn to include the chosen component in the chosen section. Components may be deleted from a fluidic scheme by simply selecting them for deletion. After a component is deleted, the diagram may be automatically redrawn to reflect the deletion.

A graphical user interface similar to graphical user interface 1300 may be especially useful for the placement of certain components to a selected fluidic scheme, regardless of how the fluidic scheme was selected. For example, air sensors are often used in chromatography setups to detect the presence of air in the flow lines. Because air is highly detrimental to the operation of the system, its detection is important, and an experiment may be stopped when air is detected. Air detectors typically mount outside of fluid lines in the system, and are especially useful in certain locations, such as immediately before the columns. In some embodiments, logical locations for air sensors may be highlighted in the selected fluidic scheme.

Figure 14:
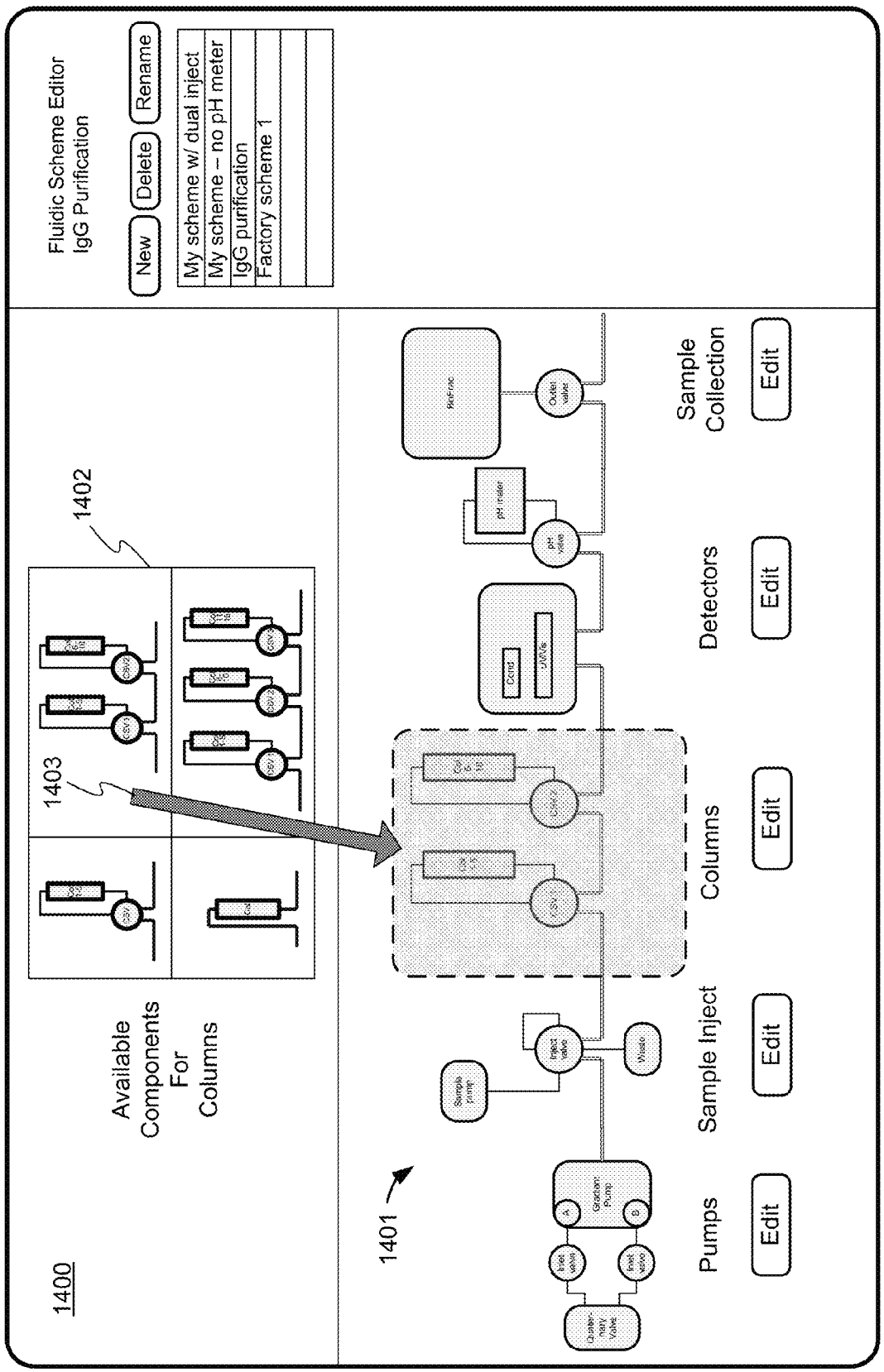
FIG. 14 illustrates a graphical user interface in accordance with another embodiment of the invention.

FIG. 14 illustrates a graphical user interface 1400 in accordance with another embodiment of the invention. Like graphical user interfaces 400 and 1300, graphical user interface 1400 uses a set of category regions into which selectable items are placed to define a process configuration. However, graphical user interface 1400 uses a different technique for selecting the items.

In the example of FIG. 14, a fluidic scheme 1401 is displayed for configuration, and includes five category regions similar to those previously discussed in the context of a chromatography system. To select a particular item to place in one of the category regions, a user may designate one of the category regions, for example by clicking an "Edit" button associated with a particular category region, by clicking within the category region, or by some other technique. In FIG. 14, the "Columns" category region has been designated, and is highlighted. In response to the category region being designated, the system presents a table 1402, listing the available items or components that are appropriate for placement in the designated category region. In the example of FIG. 14, four different column configurations are presented in table 1402. A user may then indicate which of the items from table 1402 should be placed into fluidic scheme 1401 in the highlighted category region. For example, a user may click on one of the entries in table 1402, or may "click and drag" one of the items as indicated by arrow 1403.

The other category regions may be specified in a similar manner. The user may specify the items in the category regions in any order, and may revisit the specifications if desired.

Other kinds of user interfaces may be utilized, within the scope of the appended claims.

As is discussed above, in embodiments where the computer used to select a fluidic scheme for a chromatography experiment is also connected to the configurable chromatography system used to conduct the experiment, the computer may assist in the plumbing or other setup of the system, and also in the operation of the system. In order to enable these kinds of interactions, the modules of the chromatography system are associated with or "mapped" to items in a graphical user interface such as those described above.

For example, in the system of FIG. 3 using the user interface of FIG. 4, computer 13 may interrogate the modules 11 installed in mounting frame 12 to identify what modules are present, and then enter into a table or other data structure associations between items in user interface 400 and modules mounted in mounting frame 12. If all of the modules are unique and all of the required modules for a particular fluidic scheme are present in mounting frame 12 without any additional modules being present, the mapping task is simple, as there is no ambiguity about which module should be mapped to which item in the fluidic scheme.

However, there may be ambiguity or other issues, and computer 13 is preferably configured to assist the user with resolving any difficulties in the mapping process. In one situation, if a component selected for the fluidic scheme is not present within mounting frame 12, computer 13 may recognize the fact that the selected fluidic scheme cannot be constructed with the modules available in mounting frame 12, and may alert the user. For example, the pertinent portion of the fluidic scheme may be highlighted in red, or otherwise indicated to be unavailable among the modules in mounting frame 12. The user can then locate the correct module and insert it into mounting frame 12, or may adjust the fluidic scheme to another workable configuration that uses only the available modules.

In another situation, a particular fluidic scheme may require the use of several identical components, for example inlet valves. Even if the correct number and type of inlet valves are present in mounting frame 12, computer 13 may not automatically map the inlet valves to the fluidic scheme, but may require user input to identify which physical valve should be mapped to which item in the fluidic scheme.

Figure 15:
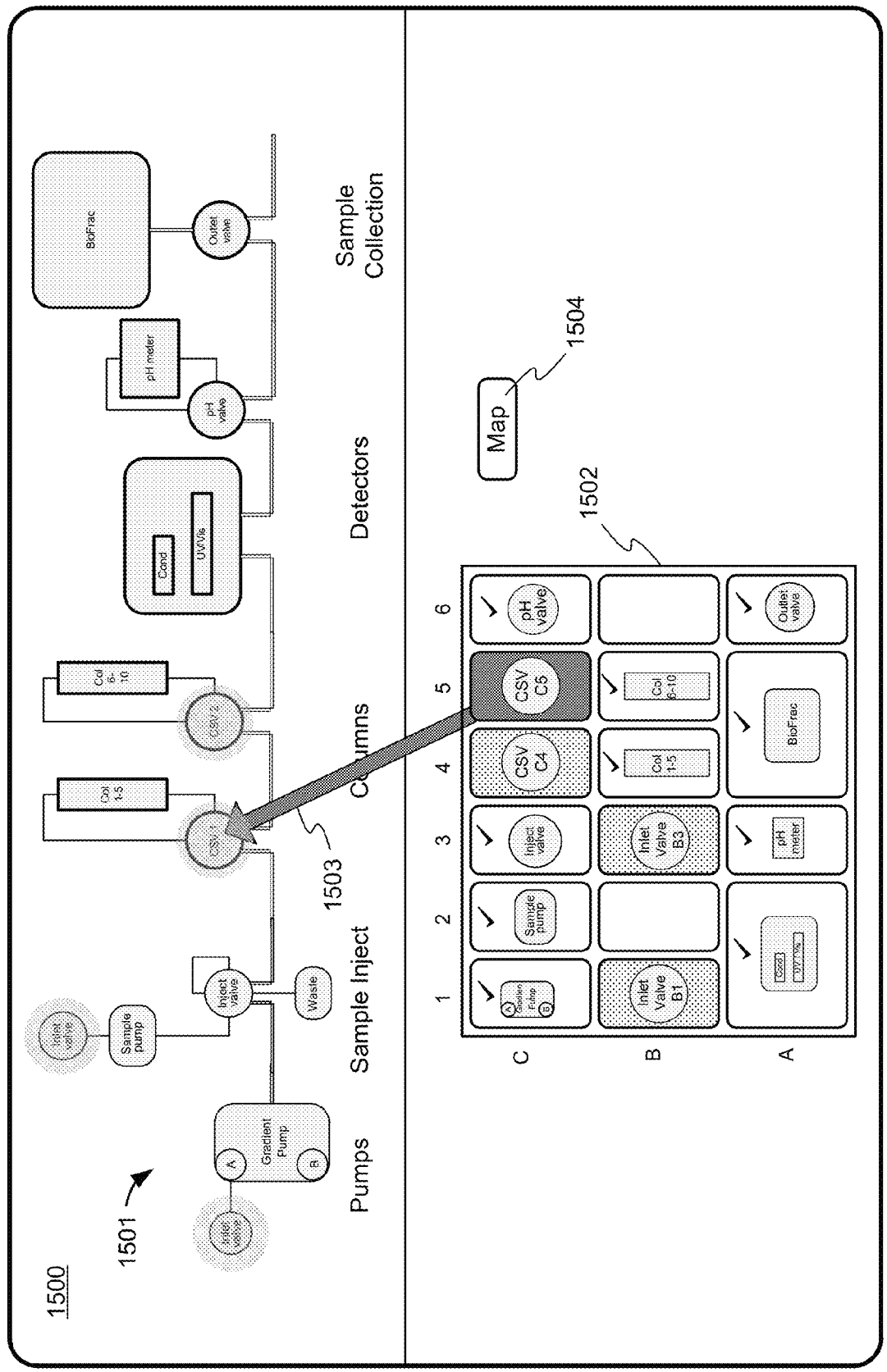
FIG. 15 illustrates a graphical user interface for assisting with a mapping process, in accordance with embodiments of the invention.

FIG. 15 illustrates a graphical user interface 1500 for assisting with the mapping process, in accordance with embodiments of the invention. As shown in FIG. 15, a fluidic scheme 1501 has been selected, for example using a technique similar to that shown in FIG. 4, FIG. 13, or FIG. 14. Graphical user interface 1500 also displays a graphical representation 1502 of a mounting frame such as mounting frame 12, including a representation of the layout of the mounting frame bays. In the example shown in FIG. 15, computer 13 has polled or otherwise identified the modules in the mounting frame, and has automatically mapped those that unambiguously correspond to items in fluidic scheme 1501.

However, fluidic scheme 1501 includes two identical column switching valves, labeled "CSV 1" and "CSV 2". Two column switching valves are present in the mounting frame, in bays C4 and C5, but computer 13 may not be able to determine which physical valve module should be mapped to which item in fluidic scheme 1501. Similarly, fluidic scheme 1501 includes two identical inlet valves, one each in the "Pumps" and "Sample Inject" sections of fluidic scheme 1501. Two inlet valves have been identified in the mounting frame, in bays B1 and B3, but computer 13 may not be able to determine their proper mapping to fluidic scheme 1501. These ambiguities are indicated in graphical user interface 1500 by highlighting the two inlet valves and the two column switching valves in fluidic scheme, and highlighting bays B1, B3, C4, and C5 in the representation 1502 of the mounting frame. Many other ways may be envisioned of indicating ambiguities to be resolved, for example using color, lists, tables, or other elements within graphical user interface 1500.

Computer 13, using graphical user interface 1500, enables the user to resolve the ambiguities. For example, the user may click and drag one of the component representations to a location within fluidic scheme 1501, as shown by arrow 1503. In some embodiments, the dragging may proceed in the opposite direction, or either direction may be effective. Computer 13 would then update its internal table or other mapping data structure, and indicate that the column switching valve represented in bay C5 has been mapped. Computer 13 may then automatically map the column switching valve represented in bay C4 to the other column switching valve shown in fluidic scheme 1501. A similar process may be used to map the ambiguous inlet valves.

Other graphical methods of resolving ambiguities may be utilized as well. For example, a user could click on one of the column switching valves represented in fluidic scheme 1501 and click on one of the column switching valves shown in mounting frame representation 1502, and then click "Map" button 1504 to indicate that the two selected items should be mapped together.

Once the mapping of modules in the mounting frame to the items shown in the selected fluidic scheme, computer 13 has the information needed to guide the user in the plumbing of the system, and to control and monitor the system during operation, as described above.

Figure 16:
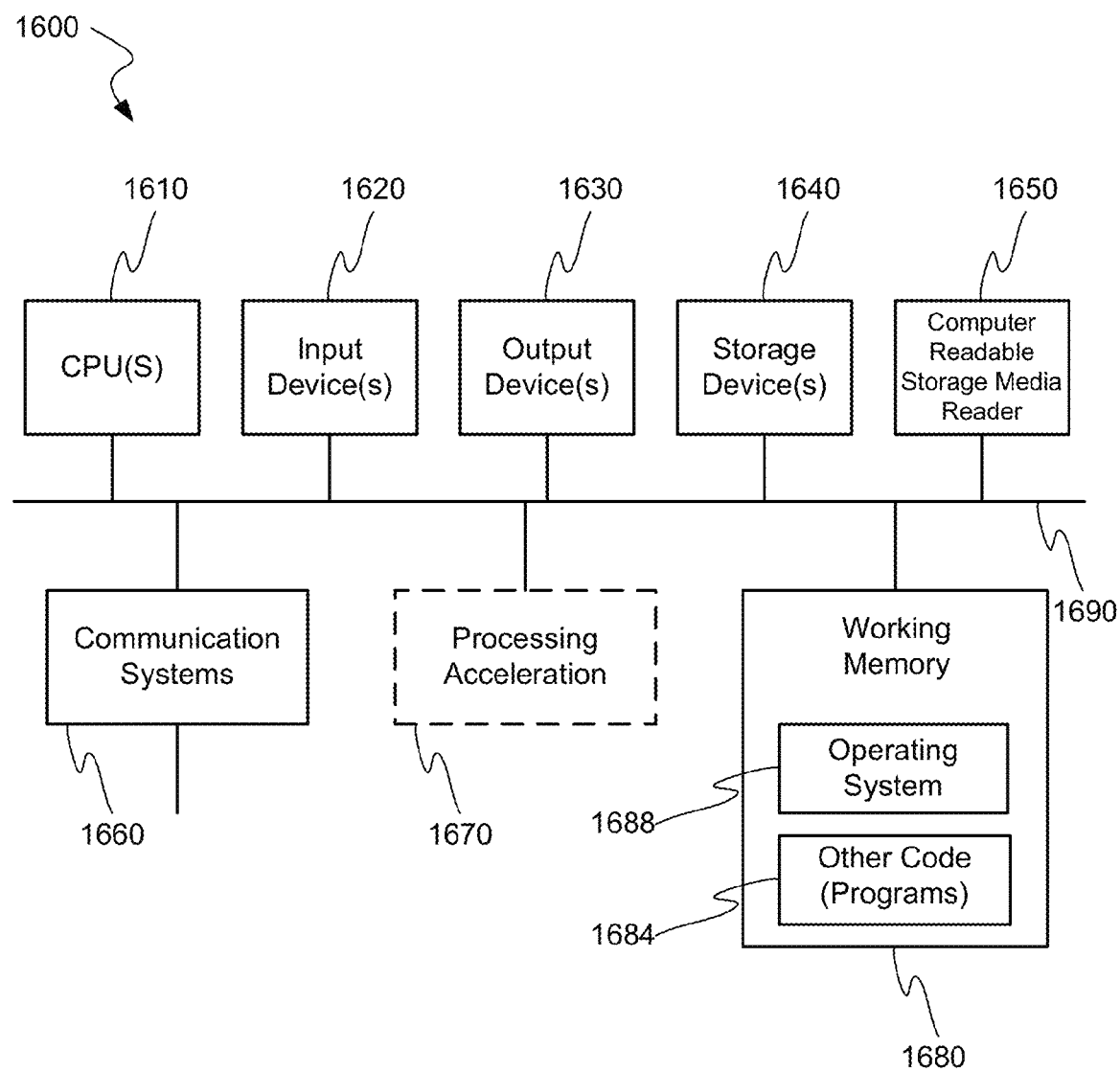
FIG. 16 is a block diagram illustrating an exemplary computer system in which embodiments of the present invention may be implemented.

FIG. 16 is a block diagram illustrating an exemplary computer system 1600 in which embodiments of the present invention may be implemented. This example illustrates a computer system 1600 such as may be used, in whole, in part, or with various modifications, to provide the functions of computer system 13 and/or other components of the invention.

Computer system 1600 is shown comprising hardware elements that may be electrically coupled via a bus 1690. The hardware elements may include one or more central processing units 1610, one or more input devices 1620 (e.g., a mouse, a keyboard, touchscreen etc.), and one or more output devices 1630 (e.g., a display device, a touchscreen, a printer, etc.). Computer system 1600 may also include one or more storage devices 1640. By way of example, storage device(s) 1640 may be disk drives, optical storage devices, solid-state storage devices such as a random access memory ("RAM") and/ or a read-only memory ("ROM"), which can be programmable, flash-updateable and/or the like.

Computer system 1600 may additionally include a computer-readable storage media reader 1650, a communications system 1660 (e.g., a modem, a network card (wireless or wired), an infra-red communication device, a device having a BLUETOOTH™ wireless communication interface, a cellular communication device, etc.), and working memory 1680, which may include RAM and ROM devices as described above. In some embodiments, computer system 1600 may also include a processing acceleration unit 1670, which can include a digital signal processor, a special-purpose processor and/or the like. Working memory 1680 may hold instructions that, when executed by CPU(S) 1610 cause computer system 1600 to perform aspects of the claimed invention.

Computer-readable storage media reader 1650 can further be connected to a computer-readable storage medium, together (and, optionally, in combination with storage device(s) 1640) comprehensively representing remote, local, fixed, and/or removable storage devices plus storage media for temporarily and/or more permanently containing computer-readable information. Communications system 1660 may permit data to be exchanged with a network, system, computer and/or other component described above.

Computer system 1600 may also comprise software elements, shown as being currently located within a working memory 1680, including an operating system 1684 and/or other code 1688. It will be appreciated that alternate embodiments of computer system 1600 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of computer system 1600 may include code 1688 for implementing any or all of the function of the various elements of the architecture as described herein.

The invention has now been described in detail for the purposes of clarity and understanding. However, those skilled in the art will appreciate that certain changes and modifications may be practiced within the scope of the appended claims.

What is claimed is:

1. A graphical user interface generated by a processor and displayed on an electronic display screen for selecting from a plurality of available process configurations, the graphical user interface comprising:
a plurality of adjacent category regions for displaying representing sections of a process
for each of the category regions, a plurality of dynamically selectable items representing different types of a respective component appropriate for placement in the respective represented section of the process being configured, and a control that causes selection of one of the selectable items and placement of the selected item into the respective one of the category regions;
wherein the set of items currently selected in the plurality of category regions defines a selected process configuration.

2. The graphical user interface of claim 1, wherein when one of the selectable items is selected, candidate locations are indicated within the category regions where the particular selected item would be appropriately placed.

3. The graphical user interface of claim 1, wherein the control comprises, for each of the category regions, a scrolling control that causes a set of selectable items appropriate for placement in the respective category region to scroll through the category region.

4. The graphical user interface of claim 3, wherein the category regions are arranged horizontally.

5. The graphical user interface of claim 1, wherein the scrolling control for each category region causes the items for the respective category region to scroll circularly.

6. The graphical user interface of claim 1, wherein the graphical user interface comprises, for each of the displayed category regions, two scrolling controls that cause the selectable items appropriate for placement in the respective category region to scroll through the respective category region, the first control causing the selectable items to scroll through the respective category region in a first direction, and the second control causing the selectable items to scroll through the respective category region in a second direction opposite the first.

7. The graphical user interface of claim 1, wherein the category regions represent respective sections of a flow diagram for a chromatography system, and the selectable items graphically represent components of a chromatography system appropriate for placement in the respective sections.

8. The graphical user interface of claim 7, wherein the graphical user interface comprises five category regions corresponding to the following sections of a flow diagram for a chromatography system: pumps, sample injection, columns, detectors, and sample collection.

9. The graphical user interface of claim 8, further comprising, during operation of a chromatography system represented in the graphical user interface by a selected configuration, status information about the operation of one or more components of the chromatography system displayed adjacent the corresponding representations of the one or more components in the graphical user interface.

10. The graphical user interface of claim 1, wherein upon designation of a particular category region, items appropriate for inclusion in the designated category region are presented to the user for selection.

11. A computer system, comprising:
a processor;
a display device;
a user input device; and
a memory holding instructions that when executed by the processor cause the computer to display, on the display device:
a plurality of adjacent category regions for displaying representing sections of a process; and
for each of the category regions, a plurality of dynamically selectable items representing different types of a respective component appropriate for placement in the respective represented section of the process, and a control that causes selection of one of the selectable items and placement of the selected item into the respective one of the category regions;
wherein the set of items currently selected in the plurality of category regions defines a selected process configuration.

12. A system, comprising:
a chromatography system comprising a plurality of fluid manipulation components configurable into a chromatography flow scheme; and
a computer system coupled to the chromatography system, the computer system including a processor, a display device, a user input device, and a memory holding instructions that when executed by the processor cause the computer to display, on the display device:
a plurality of adjacent category regions for displaying representing sections of a chromatography flow scheme; and
for each of the category regions, a plurality of dynamically selectable items appropriate for placement in the respective represented section, and a control that, in response the user input device, causes selection of one of the selectable items and placement of the selected item into one of the category regions;

wherein the set of items currently selected in the plurality of category regions defines a selected fluidic scheme.

13. The system of claim 12, wherein the selected fluidic scheme matches the configuration of the chromatography system.

14. The system of claim 12, wherein the control comprises, for each of the category regions, a scrolling control that causes a set of selectable items appropriate for placement in the respective category region to scroll through the category region.

15. The system of claim 12, wherein the instructions further cause the computer system to display, during operation of the chromatography system, status information about the operation of one or more of the fluid manipulation components, wherein the status information is displayed adjacent the corresponding representations of the one or more fluid manipulation components.

16. The system of claim 12, wherein the instructions further cause the computer system to guide a user of the system in making fluidic connections among the plurality of fluid manipulation components.

17. The system of claim 16, wherein the instructions further cause the computer system to communicate to at least one of the fluid manipulation components an instruction to visibly indicate a point of connection for a fluidic connection.

18. The system of claim 12, wherein the instructions further cause the computer system to interact with the plurality of fluid manipulation components to identify the fluid manipulation components, and to map in a data structure at least one of the fluid manipulation components with a particular item in the selected fluidic scheme.

19. The system of claim 18, wherein the instructions further cause the computer system to indicate in a graphical user interface at least one ambiguity in the mapping of fluid manipulation components to items in the graphical user interface.

20. A graphical user interface generated by a processor and displayed on an electronic display screen for mapping components of a chromatography system to a representation of a fluidic scheme, the graphical user interface comprising:

a representation of the fluidic scheme including representations of a plurality of fluid manipulation components needed to implement the fluidic scheme;

a representation of a chromatography system that includes a plurality of actual fluid manipulation components;

and an indication of at least one ambiguity in the mapping of the actual fluid manipulation components to the fluid manipulation component representations, wherein the at least one ambiguity arises from the inclusion of multiple identical fluid manipulation components in the fluidic scheme.

21. The graphical user interface of claim 20, further comprising a user interface device that enables a user to resolve the at least one ambiguity.

22. The graphical user interface of claim 21, wherein the user interface device enables the user to drag a representation of a fluid manipulation component from the representation of the fluidic scheme to the representation of the chromatography system, or the user interface component enables the user to drag a representation of a fluid manipulation component from the representation of the chromatography system to the representation of the fluidic scheme chromatography system, or both.

* * * * *